United States Patent [19]

Enomoto et al.

[11] Patent Number: 5,314,864
[45] Date of Patent: May 24, 1994

[54] N-AMINOURACIL DERIVATIVES, AND THEIR PRODUCTION AND USE

[75] Inventors: Masayuki Enomoto, Nishinomiya; Eiki Nagano, Itami; Ryo Sato; Masaharu Sakaki, both of Toyonaka, all of Japan

[73] Assignee: Sumitomo Chemical Company, Limited, Osaka, Japan

[21] Appl. No.: 947,978

[22] Filed: Sep. 21, 1992

Related U.S. Application Data

[63] Continuation of Ser. No. 742,021, Aug. 8, 1991, abandoned, which is a continuation-in-part of Ser. No. 586,229, Sep. 21, 1990, abandoned.

[30] Foreign Application Priority Data

Sep. 26, 1989 [JP] Japan .................................. 1-250320
May 24, 1990 [JP] Japan .................................. 2-136498

[51] Int. Cl.$^5$ ..................... C07D 498/00; A01N 43/84
[52] U.S. Cl. ..................................... 504/225; 544/105
[58] Field of Search ......................... 544/105; 504/225

[56] References Cited

U.S. PATENT DOCUMENTS

| | | | |
|---|---|---|---|
| 3,920,653 | 11/1975 | Wenzelburger et al. | 544/311 |
| 4,619,687 | 10/1986 | Haga et al. | 71/92 |
| 4,640,707 | 2/1987 | Nagano et al. | 71/96 |
| 4,670,042 | 6/1987 | Haga et al. | 71/92 |
| 4,746,352 | 5/1988 | Wenger et al. | 71/90 |
| 4,812,164 | 3/1989 | Wenger et al. | 71/92 |
| 4,859,229 | 8/1989 | Wenger et al. | 71/92 |
| 4,877,444 | 10/1989 | Enomoto et al. | 71/92 |
| 4,885,024 | 12/1989 | Enomoto et al. | 71/92 |
| 4,981,508 | 1/1991 | Strunk et al. | 71/92 |

FOREIGN PATENT DOCUMENTS

| | | |
|---|---|---|
| 56415 | of 1990 | Australia . |
| 0311135 | 10/1987 | European Pat. Off. . |
| 0328001 | 8/1989 | European Pat. Off. . |
| 0408382 | 1/1991 | European Pat. Off. . |
| 1139580 | 11/1987 | Japan . |
| 8902891 | 1/1987 | World Int. Prop. O. . |
| 8810254 | 6/1987 | World Int. Prop. O. . |
| 90/15057 | 12/1990 | World Int. Prop. O. . |

Primary Examiner—Mukund J. Shah
Assistant Examiner—Matthew V. Grumbling
Attorney, Agent, or Firm—Birch, Stewart, Kolasch & Birch

[57] ABSTRACT

A compound of the formula:

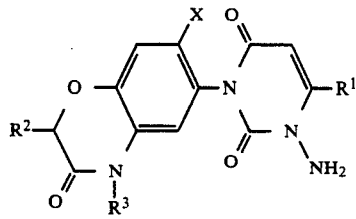

wherein $R^1$ is a trifluoromethyl group or a pentafluoroethyl group, $R^2$ is a hydrogen atom or a methyl group, $R^3$ is a $C_1$–$C_7$ alkyl group, a $C_3$–$C_7$ alkenyl group, a $C_3$–$C_7$ alkynyl group, a halo($C_1$–$C_6$)alkyl group, a halo($C_3$–$C_6$)alkenyl group or a $C_1$–$C_4$ alkoxy($C_1$–$C_3$)alkyl group and X is a hydrogen atom or a fluorine atom, which is useful as a herbicide.

18 Claims, No Drawings

N-AMINOURACIL DERIVATIVES, AND THEIR PRODUCTION AND USE

This application is a continuation of application Ser. No. 07/742,021 filed on Aug. 8, 1991, now abandoned, which is a continuation-in-part of Ser. No. 07/586,229 filed on Sep. 21, 1990, now abandoned.

The present invention relates to N-aminouracil derivatives, and their production and use. More particularly, it relates to N-aminouracil derivatives, a process for producing them, and their use as herbicides.

U.S. Pat. No. 3,920,653 discloses some N-aminouracil derivatives useful as herbicides. However, these known herbicides are not sufficient in herbicidal potency or have poor selectivity between crop plants and weeds. Their herbicidal activity is thus not necessarily satisfactory.

It has now been found that N-aminouracil derivatives of the formula:

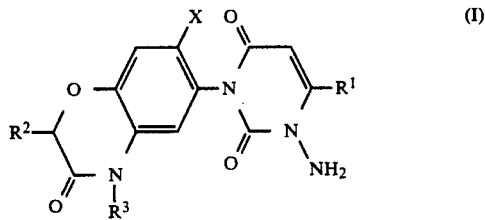

wherein $R^1$ is a trifluoromethyl group or a pentafluoroethyl group, $R^2$ is a hydrogen atom or a methyl group, $R^3$ is a $C_1$–$C_7$ alkyl group, a $C_3$–$C_7$ alkenyl group, a $C_3$–$C_7$ alkynyl group, a halo($C_1$–$C_6$)alkyl group, a halo($C_3$–$C_6$)alkenyl group or a $C_1$–$C_4$ alkoxy($C_1$–$C_3$)alkyl group and X is a hydrogen atom or a fluorine atom show a high herbicidal potency against various weeds with a high selectivity between crop plants and weeds. Thus, they produce a strong herbicidal activity against a wide variety of weeds including broad-leaved weeds, Graminaceous weeds, Commelinaceous weeds and Cyperaceous weeds in agricultural plowed fields by foliar or soil treatment without producing any material phytotoxicity on various agricultural crops such as corn, wheat, barley, rice plant, soybean and cotton. Examples of the broad-leaved weeds include wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursapastoris*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf mornigglory (*Ipomoea hederacea*), tall morningglory (*Ipomoea purpurea*), field bindweed (*Convolvulus arvensis*), henbit (*Lamium amplexicaure*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata*), corn marigold (*Chrysanthemum segetum*), purple deadnettle (*Lamium purpureum*), sun spurge (*Euphorbia helioscopia*), spotted spurge (*Euphorbia maculata*), etc.

Examples of Graminaceous weeds include Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), bermudagrass (*Cynodon dactylon*), downy brome (*Bromus tectorum*), giant foxtail (*Setaria faberi*), etc. Example of Commelinaceous weeds include asiatic dayflower (*Commelina communis*), etc. Examples of Cyperaceous weeds include rice flatsedge (*Cyperus iria*), purple nutsedge (*Cyperus rotundus*), etc.

The N-aminouracil derivatives (I) of the invention are also effective in exterminating paddy field weeds including Graminaceous weeds such as barnyardgrass (*Echinochloa oryzicola*), broad-leaved weeds such as common falsepimpernel (*Lindernia procumbens*), indian toothcup (*Rotala indica*) and waterwort (*Elatine triandra*), Cyperaceous weeds such as water nutgrass (*Cyperus serotinus*), hardstem bulrush (*Scirpus juncoides*), needle spikerush (*Eleocharis acicularis*) and umbrella sedge (*Cyperus difformis*), and others such as monochoria (*Monochoria vaginalis*) and arrowhead (*Sagittaria pygmaea*) without producing any phytotoxicity to rice plants on flooding treatment.

Among the compounds (I), preferred are those wherein $R^1$ is as defined above, $R^2$ is a hydrogen atom, $R^3$ is a $C_3$–$C_4$ alkynyl group and X is a fluorine atom.

Typical examples of the preferred compounds are 3-amino-1-[7-fluoro-4-propargyl-2H-1,4-bezoxazin-3(4H)-on-6-yl]-4-trifluoromethyl-1,2,3,6-tetrahydropyrimidine-2,6-dione and 3-amino-1-[7-fluoro-4-(1-methylpropargyl)-2H-1,4-benzoxazin-3(4H)-on-6-yl]-4-trifluoromethyl-1,2,3,6-tetrahydropyrimidine-2,6-dione.

The compound (I) of the invention can be produced by reacting a compound of the formula:

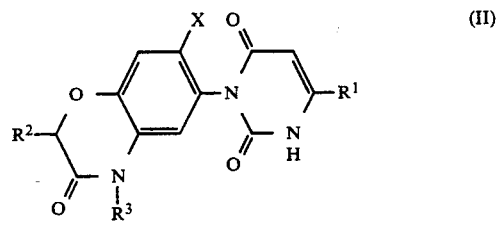

wherein $R^1$, $R^2$, $R^3$ and X are each as defined above with an aminating agent.

The reaction is usually carried out in an inert solvent at a temperature of about 0° to 100° C. for a period of about 0.5 to 10 hours.

The aminating agent is used in an amount of about 1 to 1.2 equivalents to one equivalent of the compound (II). As the aminating agent, there may be used 2,4-dinitrophenoxyamine, O-mesitylsulfonyl hydroxylamine or the like.

Examples of the inert solvent are aliphatic hydrocarbons (e.g. hexane, heptane, ligroin, petroleum ether), aromatic hydrocarbons (e.g. benzene, toluene, xylene), ethers (e.g. diethyl ether, diisopropyl ether, dioxane, tetrahydrofuran, diethylene glycol dimethyl ether), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethylsulfoxide, sulphorane), etc. These may be used solely or in combination.

After completion of the reaction, the reaction mixture is subjected to ordinary post-treatment. For instance, the reaction mixture is poured into water and extracted with an organic solvent, followed by concentration. If desired, any conventional purification procedure such as chromatography, distillation or recrystallization may be applied to the resulting product.

According to the above procedure, the compounds (I) as shown Table 1 are obtained.

TABLE 1

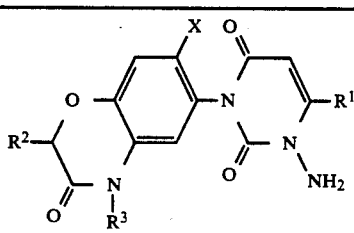

(I)

| $R^1$ | $R^2$ | $R^3$ | X |
|---|---|---|---|
| $CF_3$ | H | $CH_3$ | F |
| $CF_3$ | H | $C_2H_5$ | F |
| $CF_3$ | H | $(n)C_3H_7$ | F |
| $CF_3$ | H | $(i)C_3H_7$ | F |
| $CF_3$ | H | $(n)C_4H_9$ | F |
| $CF_3$ | H | $(s)C_4H_9$ | F |
| $CF_3$ | H | $(i)C_4H_9$ | F |
| $CF_3$ | H | $(n)C_5H_{11}$ | F |
| $CF_3$ | H | $(n)C_6H_{13}$ | F |
| $CF_3$ | H | $(n)C_7H_{15}$ | F |
| $CF_3$ | H | $CH_2CH=CH_2$ | F |
| $CF_3$ | H | $CH_2C(H)=C(CH_3)H$ | F |
| $CF_3$ | H | $CH_2C(H)=C(CH_3)H$ (H,H) | F |
| $CF_3$ | H | $CH_2CH=C(CH_3)_2$ | F |
| $CF_3$ | H | $CH_2C(CH_3)=CH_2$ | F |
| $CF_3$ | H | $CH_2C(H)=C(CH_3)(CH_3)$ (H₃C, CH₃) | F |
| $CF_3$ | H | $CH_2C(H_3C)=C(CH_3)H$ | F |
| $CF_3$ | H | $CH(CH_3)CH=CH_2$ | F |
| $CF_3$ | H | $CH(CH_3)C(H)=C(H)CH_3$ | F |
| $CF_3$ | H | $CH(CH_3)C(H)=C(H)CH_3$ (alt) | F |
| $CF_3$ | H | $CH(CH_3)CH=CH(CH_3)$ | F |

TABLE 1-continued

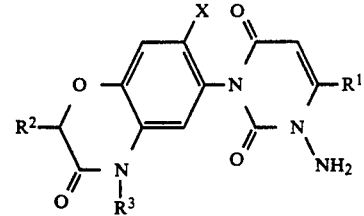

(I)

| $R^1$ | $R^2$ | $R^3$ | X |
|---|---|---|---|
| $CF_3$ | H | $CH(CH_3)C(CH_3)=C(H)H_3C$ | F |
| $CF_3$ | H | $CH(CH_3)C(H)=C(CH_3)CH_3$ | F |
| $CF_3$ | H | $CH_2C\equiv CH$ | F |
| $CF_3$ | H | $CH(CH_3)C\equiv CH$ | F |
| $CF_3$ | H | $CH_2C\equiv CCH_3$ | F |
| $CF_3$ | H | $CH(CH_3)C\equiv CCH_3$ | F |
| $CF_3$ | H | $CH_2C\equiv CC_2H_5$ | F |
| $CF_3$ | H | $CH_2C\equiv CC_3H_7$ | F |
| $CF_3$ | H | $CH(CH_3)C\equiv CC_2H_5$ | F |
| $CF_3$ | H | $CH(CH_3)C\equiv CC_3H_7$ | F |
| $CF_3$ | H | $CH_2CH_2F$ | F |
| $CF_3$ | H | $CH_2CF_3$ | F |
| $CF_3$ | H | $CH_2C(H)=C(H)Cl$ | F |
| $CF_3$ | H | $CH_2C(Cl)=CH_2$ | F |
| $CF_3$ | H | $CH_2C(Br)=CH_2$ | F |
| $CF_3$ | H | $CH_2C(H)=C(H)F$ | F |
| $CF_3$ | H | $CH_2C(F)=CH_2$ | F |
| $CF_3$ | H | $CH_2OCH_3$ | F |
| $CF_3$ | H | $C_2H_4OCH_3$ | F |
| $CF_3$ | H | $CH_2OC_2H_5$ | F |
| $CF_3$ | H | $CH(CH_3)OCH_3$ | F |

TABLE 1-continued

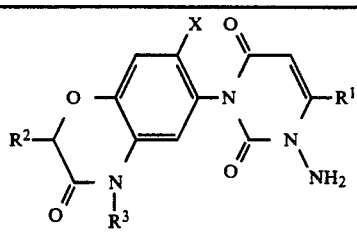

(I)

| R¹ | R² | R³ | X |
|---|---|---|---|
| CF₃ | H | CHOC₂H₅ / CH₃ | F |
| CF₃ | CH₃ | CH₃ | F |
| CF₃ | CH₃ | C₂H₅ | F |
| CF₃ | CH₃ | (n)C₃H₇ | F |
| CF₃ | CH₃ | (n)C₄H₉ | F |
| CF₃ | CH₃ | CH₂CH=CH₂ | F |
| CF₃ | CH₃ | CHCH=CH₂ / CH₃ | F |
| CF₃ | CH₃ | CH₂C=CH / H CH₃ | F |
| CF₃ | CH₃ | CH₃ / CHC=CH / H CH₃ | F |
| CF₃ | CH₃ | CH₂C≡CH | F |
| CF₃ | CH₃ | CHC≡CH / CH₃ | F |
| CF₃ | CH₃ | CH₂CH₂F | F |
| CF₃ | CH₃ | CH₂OCH₃ | F |
| CF₃ | CH₃ | CHOCH₃ / CH₃ | F |
| CF₃ | H | C₂H₅ | H |
| CF₃ | H | (n)C₃H₇ | H |
| CF₃ | H | CH₂CH=CH₂ | H |
| CF₃ | H | CHCH=CH₂ / CH₃ | H |
| CF₃ | H | CH₂C≡CH | H |
| CF₃ | H | CHC≡CH / CH₃ | H |
| CF₃ | H | CH₂CH₂F | H |
| CF₃ | H | CH₂OCH₃ | H |
| CF₃ | H | CHOCH₃ / CH₃ | H |
| CF₃ | H | CH₂OC₂H₅ | H |
| C₂F₅ | H | CH₃ | F |
| C₂F₅ | H | C₂H₅ | F |
| C₂F₅ | H | (n)C₃H₇ | F |
| C₂F₅ | H | (i)C₃H₇ | F |
| C₂F₅ | H | (n)C₄H₉ | F |
| C₂F₅ | H | (s)C₄H₉ | F |
| C₂F₅ | H | (i)C₄H₉ | F |
| C₂F₅ | H | (n)C₅H₁₁ | F |
| C₂F₅ | H | (n)C₆H₁₃ | F |

TABLE 1-continued

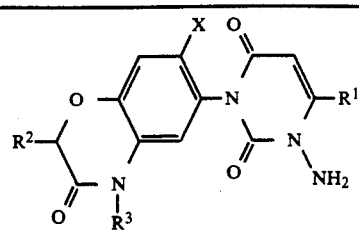

(I)

| R¹ | R² | R³ | X |
|---|---|---|---|
| C₂F₅ | H | (n)C₇H₁₅ | F |
| C₂F₅ | H | CH₂CH=CH₂ | F |
| C₂F₅ | H | CH₂C=CH / H CH₃ | F |
| C₂F₅ | H | CH₂C=CCH₃ / H H | F |
| C₂F₅ | H | CH₂CH=C(CH₃)₂ | F |
| C₂F₅ | H | CH₂C=CH₂ / CH₃ | F |
| C₂F₅ | H | CH₂C=CH / H₃C CH₃ | F |
| C₂F₅ | H | CH₂C=CCH₃ / H₃C H | F |
| C₂F₅ | H | CH₃ / CHCH=CH₂ | F |
| C₂F₅ | H | CH₃ / CHC=CH / H CH₃ | F |
| C₂F₅ | H | CH₃ / CHC=CCH₃ / H H | F |
| C₂F₅ | H | CH₃ / CHC=CH₂ / CH₃ | F |
| C₂F₅ | H | CH₃ / CHC=CCH₃ / H₃C H | F |
| C₂F₅ | H | CH₃ / CHC=CH / H₃C CH₃ | F |
| C₂F₅ | H | CH₂C≡CH | F |
| C₂F₅ | H | CHC≡CH / CH₃ | F |
| C₂F₅ | H | CH₂C≡CCH₃ | F |

TABLE 1-continued

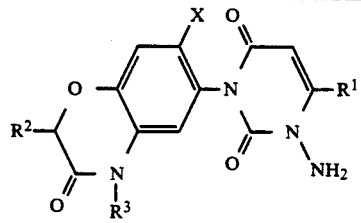

(I)

| R¹ | R² | R³ | X |
|---|---|---|---|
| $C_2F_5$ | H | CHC≡CCH₃ / CH₃ | F |
| $C_2F_5$ | H | CH₂C≡CC₂H₅ | F |
| $C_2F_5$ | H | CH₂C≡CC₃H₇ | F |
| $C_2F_5$ | H | CHC≡CC₂H₅ / CH₃ | F |
| $C_2F_5$ | H | CHC≡CC₃H₇ / CH₃ | F |
| $C_2F_5$ | H | CH₂CH₂F | F |
| $C_2F_5$ | H | CH₂CF₃ | F |
| $C_2F_5$ | H | CH₂C=CH / H Cl | F |
| $C_2F_5$ | H | CH₂C=CH₂ / Cl | F |
| $C_2F_5$ | H | CH₂C=CH₂ / Br | F |
| $C_2F_5$ | H | CH₂C=CH / H F | F |
| $C_2F_5$ | H | CH₂C=CH₂ / F | F |
| $C_2F_5$ | H | CH₂OCH₃ | F |
| $C_2F_5$ | H | C₂H₄OCH₃ | F |
| $C_2F_5$ | H | CH₂OC₂H₅ | F |
| $C_2F_5$ | H | CHOCH₃ / CH₃ | F |
| $C_2F_5$ | H | CHOC₂H₅ / CH₃ | F |
| $C_2F_5$ | CH₃ | CH₃ | F |
| $C_2F_5$ | CH₃ | C₂H₅ | F |
| $C_2F_5$ | CH₃ | (n)C₃H₇ | F |
| $C_2F_5$ | CH₃ | (n)C₄H₉ | F |
| $C_2F_5$ | CH₃ | CH₂CH=CH₂ | F |
| $C_2F_5$ | CH₃ | CHCH=CH₂ / CH₃ | F |
| $C_2F_5$ | CH₃ | CH₂C=CH / H CH₃ | F |

TABLE 1-continued

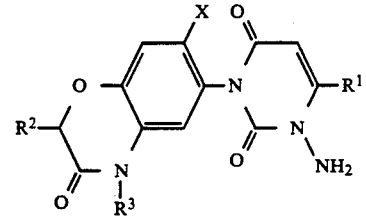

(I)

| R¹ | R² | R³ | X |
|---|---|---|---|
| $C_2F_5$ | CH₃ | CHC=CH / H CH₃ | F |
| $C_2F_5$ | CH₃ | CH₂C≡CH | F |
| $C_2F_5$ | CH₃ | CHC≡CH / CH₃ | F |
| $C_2F_5$ | CH₃ | CH₂CH₂F | F |
| $C_2F_5$ | CH₃ | CH₂OCH₃ | F |
| $C_2F_5$ | CH₃ | CHOCH₃ / CH₃ | F |
| $C_2F_5$ | H | C₂H₅ | H |
| $C_2F_5$ | H | (n)C₃H₇ | H |
| $C_2F_5$ | H | CH₂CH=CH₂ | H |
| $C_2F_5$ | H | CHCH=CH₂ / CH₃ | H |
| $C_2F_5$ | H | CH₂C≡CH | H |
| $C_2F_5$ | H | CHC≡CH / CH₃ | H |
| $C_2F_5$ | H | CH₂CH₂F | H |
| $C_2F_5$ | H | CH₂OCH₃ | H |
| $C_2F_5$ | H | CHOCH₃ / CH₃ | H |
| $C_2F_5$ | H | CH₂OC₂H₅ | H |

Some of the compounds (I) have optical isomers, which are also included within the scope of the invention.

The starting compound (II) may be produced according to the following scheme:

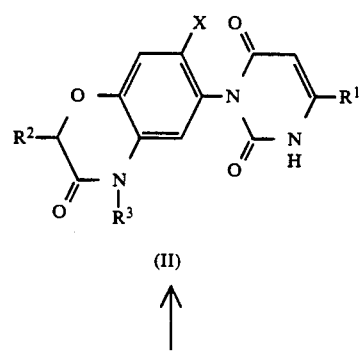

(II)

-continued

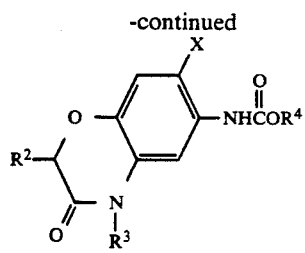

(III)

↑

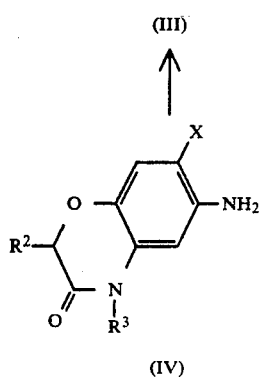

(IV)

wherein $R^4$ is a $C_1$–$C_6$ alkyl group and $R^1$, $R^2$, $R^3$ and $X$ are each as defined above.

The reaction at each step n the above scheme will be hereinafter explained in detail.

(1) Preparation of the compound (II) from the compound (III):

The compound (II) may be produced by reacting the compound (III) with a compound of the formula:

$$R^1(NH_2)C=CHCOOR^5 \quad (V)$$

wherein $R^5$ is a $C_1$–$C_6$ alkyl group and $R^1$ is as defined above usually in the presence of a dehydrogenating agent in an inert solvent at a temperature of about 0° to 200° C. for a period of about 0.5 to 10 hours.

In general, the compound (V) and the dehydrogenating agent are used respectively in amounts of about 1 to 1.2 equivalents and of about 1 to 1.2 equivalents to one equivalent of the compound (III). As the dehydrogenating agent, there may be used an inorganic base (e.g. sodium carbonate, potassium carbonate, sodium hydride), an alkali metal alkoxide (e.g. sodium methoxide, sodium ethoxide), etc.

Examples of the inert solvent are aliphatic hydrocarbons (e.g. hexane, heptane, ligroin, petroleum ether), aromatic hydrocarbons (e.g. benzene, toluene, xylene), ethers (e.g. diethyl ether, diisopropyl ether, dioxane, tetrahydrofuran, diethylene glycol dimethyl ether), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethylsulfoxide, sulphorane), etc. These may be used solely or in combination.

After completion of the reaction, the reaction mixture is subjected to ordinary post-treatment. For instance, the reaction mixture is poured into water and extracted with an organic solvent, followed by concentration. If desired, any conventional purification procedure such as chromatography, distillation or recrystallization may be applied to the resulting product.

The compound (II) may be aminated without isolation to give the compound (I).

(2) Preparation of the compound (III) from the compound (IV):

The compound (III) may be produced by reacting the compound (IV) with a compound of the formula:

$$\overset{O}{\underset{\|}{ClCOR^4}} \quad (VI)$$

wherein $R^4$ is as defined above in the existence of a dehydrohalogenating agent in the presence or absence of an inert solvent at a temperature of about 0° to 150° C. for a period of about 0.5 to 10 hours.

Normally, the compound (VI) and the dehydrohalogenating agent are used respectively in amounts of about 1 to 1.5 equivalents and of about 1 to 1.5 equivalents to one equivalent of the compound (IV). As the dehydrohalogenating agent, there may be used an organic base (e.g. pyridine, triethylamine, N,N-diethylaniline), an inorganic base (e.g. sodium hydroxide, potassium hydroxide, sodium carbonate, potassium carbonate, sodium hydride), an alkali metal alkoxide (e.g. sodium methoxide, sodium ethoxide), etc.

Examples of the inert solvent are aromatic hydrocarbons (e.g. benzene, toluene, xylene), halogenated hydrocarbons (e.g. chloroform, carbon tetrachloride), ethers (e.g. diethyl ether, dioxane), etc.

After completion of the reaction, the reaction mixture is subjected to ordinary post-treatment. For instance, the reaction mixture is poured into water and extracted with an organic solvent, followed by concentration. If desired, any conventional purification procedure such as chromatography, distillation or recrystallization may be applied to the resulting product.

The compound (IV) can be produced by the method as disclosed in U.S. Pat. No. 4,640,707.

Typical embodiments for production of the compounds (I) are illustratively shown in the following Examples.

EXAMPLE 1

A mixture of 7-fluoro-6-methoxycarbonylamino-4-propargyl-2H-1,4-benzoxazin-3(4H)-one (1.4 g) and ethyl 3-amino-4,4,4-trifluorocrotonate was dissolved in dimethylformamide (5 g), and sodium hydride (0.2 g) was added thereto. The resultant mixture was stirred for 30 minutes while cooling with ice and heated under reflux for 3 hours. After cooling, 2,4-dinitrophenoxyamine (1.2 g) was added thereto, and the resultant mixture was stirred at 40° C. for 3 hours. After completion of the reaction, the reaction mixture was combined with water, extracted with ethyl acetate, dried over magnesium sulfate and concentrated under reduced pressure. The residue was purified by silica gel column chromatography to give 3-amino-1-[7-fluoro-4-propargyl-2H-1,4-benzoxazin-3(4H)-on-6yl]-4-trifluoromethyl-1,2,3,6-tetrahydropyrimidine-2,6-dione (0.2 g).

In the same manner as above, the compounds (I) as shown in Table 2 were obtained.

TABLE 2

$$\text{(I)}$$

Structure: benzoxazinone fused system with substituents X, O, R², R³, and R¹ on a pyrimidinedione with NH₂.

| Compound No. | R¹ | R² | R³ | X | Physical property |
|---|---|---|---|---|---|
| 1 | CF₃ | H | (n)C₃H₇ | F | ¹H-NMR δ ppm [CDCl₃, 60MHz] 0.91(3H, t, J=7.5Hz), 1.81-1.45(2H, m), 3.80(2H, t, J=6Hz), 4.57(2H, s), 4.70(2H, br), 6.17(1H, s), 6.78 (1H, d, J=6Hz), 6.83(1H, d, J=11Hz). |
| 2 | CF₃ | H | CH₂C≡CH | F | m.p.: 97-99° C. |
| 3 | CF₃ | H | CH₃\|CHC≡CH | F | m.p.: 93-95° C. |

A typical embodiment for preparation of the compound (II) is illustratively shown in the following example.

EXAMPLE 2

A mixture of 7-fluoro-6-methoxycarbonylamino-4-propargyl-2H-1,4-benzoxazin-3(4H)-one (1.4 g) and ethyl 3-amino-4,4,4-trifluorocrotonate was dissolved in dimethylformamide (5 g), and sodium hydride (0.2 g) was added thereto. The resultant mixture was stirred for 30 minutes while cooling with ice and heated under reflux for 3 hours. After cooling, the reaction mixture was poured into water and extracted with ethyl acetate. The organic layer was concentrated, and the residue was purified by column chromatography to give 1-[7-fluoro-4-propargyl-2H-1,4-benzoxazin-3(4H)-on-6-yl]-4-trifluoromethyl-1,2,3,6-tetrahydropyrimidine-2,6-dione (0.2 g).

In the same manner as above, the compounds (II) as shown in Table 3 were obtained.

TABLE 3

$$\text{(II)}$$

| R¹ | R² | R³ | X | Physical property |
|---|---|---|---|---|
| CF₃ | H | n-C₃H₇ | F | ¹H-NMR δ (ppm) [CDCl₃, 60MHz]: 0.8(3H, t), 1.3-1.8(2H, m), 3.7 (2H, t), 4.55(2H, s), 6.1(1H, s), 6.7(1H, d), 6.8(1H, d) |
| CF₃ | H | CH₂C≡CH | F | m.p. 51-53° C. |

A typical embodiment for production of the compound (III) is illustratively shown in the following Example.

EXAMPLE 3

A mixture of 6-amino-7-fluoro-4-propargyl-2H-1,4-benzoxazin-3(4H)-one (2.1 g), N,N-diethylaniline (1.5 g) and methyl chloroformate (1.0 g) was dissolved in 1,2-dichloroethane (10 g), and the resultant mixture was heated under reflux for 3 hours. After cooling, the reaction mixture was washed with water, and the organic layer was concentrated. The residue was washed with methanol to give 7-fluoro-6-methoxycarbonylamino-4-propargyl-2H-1,4-benzoxazin-3(4H)-one (2.0 g).

In the same manner as above, the compounds (III) as shown in Table 4 were obtained.

TABLE 4

$$\text{(III)}$$

| R² | R³ | R⁴ | X | Physical property |
|---|---|---|---|---|
| H | C₂H₅ | CH₃ | F | m.p. 141-142° C. |
| H | CH₂CH=CH₂ | CH₃ | F | m.p. 117-118° C. |
| H | CH₂C≡CH | CH₃ | F | m.p. 188-189° C. |
| H | CH₃\|CHC≡CH | CH₃ | F | m.p. 173-174° C. |
| H | CH₂C=CH₂\|Cl | CH₃ | F | m.p. 148-149° C. |
| H | (n)C₃H₇ | CH₃ | F | m.p. 99-100° C. |
| H | CH₃\|CHCH=CH₂ | CH₃ | F | m.p. 92-93° C. |
| H | CH₂C≡CH | CH₃ | H | m.p. 170-173° C. |
| CH₃ | CH₂C≡CH | CH₃ | F | m.p. 171-172° C. |

For the practical usage of the compound (I), it is usually formulated with conventional solid or liquid carriers or diluents as well as surface active agents or auxiliary agents into conventional preparation forms such as emulsifiable concentrates, wettable powders, suspensions, water dispersible granules and granules. The content of the compound (I) as the active ingredient in such preparation forms is normally within a range of about 0.02 to 80% by weight, preferably of about 0.05 to 70% by weight. Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent used for emulsification, dispersion or spreading may be of any type, for instance, either anionic or non-ionic. Example of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the present invention are illustratively shown in the following examples wherein parts are by weight. The number of the active ingredient corresponds to the one in Table 2.

FORMULATION EXAMPLE 1

Fifty parts of Compound No. 2 or 3, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Five parts of any one of Compound Nos. 1 to 3, 14 parts of polyoxyethylenestyrylphenyl ether, 6 parts of calcium dodecylbenzenesulfonate, 25 parts of xylene and 50 parts of cyclohexanone are well mixed to obtain an emulsifiable concentrate.

FORMULATION EXAMPLE 3

Two parts of any one of Compound Nos. 1 to 3, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of Compound No. 2 or 3 are mixed with 3 parts of polyoxyethylene sorbitan monooleate, 3 parts of carboxymethyl cellulose and 69 parts of water and pulverized until the particle size of the mixture becomes less than 5 microns to obtain a suspension.

FORMULATION EXAMPLE 5

0.05 Part of any one of Compound Nos. 1 to 3, 1 part of synthetic hydrous silicate, 2 parts of calcium ligninsulfonate, 30 parts of bentonite and 66.95 parts of kaolin clay are well mixed while being powdered. The mixture is then kneaded with water, granulated and dried to obtain granules.

The compound (I) thus formulated in any suitable preparation form is useful for pre-emergence or post-emergence control of undesired weeds by soil or foliar treatment as well as flood fallowing treatment. These treatments include application to the soil surface prior to or after planting, incorporation into the soil prior to planting or transplanting, etc. The foliar treatment may be effected by spraying the herbicidal composition containing the compound (I) over the top of plants. It may also be applied directly to the weeds if care is taken to keep the chemical off the crop foliage.

The compound (I) may be used together with any other herbicide to improve its activity as a herbicide, and in some cases, a synergistic effect can be expected. Further, it may be applied in combination with an insecticide, an acaricide, a nematocide, a fungicide, a plant growth regulator, a fertilizer, a soil improver, etc. It is also useful as a herbicide to be employed for orchards, pasture lands, lawns, forests, non-agricultural fields, etc.

The dosage of the compound (I) may vary depending on the prevailing weather conditions, the formulation used, the prevailing season, the mode of application, the soil involved, the crop and weed species, etc. Generally, however, the dosage is from about 0.01 to 80 grams, preferably from about 0.02 to 40 grams, of the active ingredient per are. The herbicidal composition of the invention formulated in the form of an emulsifiable concentrate, a wettable powder, a water-dispersible granule or a suspension may ordinarily be employed by diluting it with water at a volume of about 1 to 10 liters per are, if necessary with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the compound (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4, or 5, the numeral "0" indicating no material difference as seen in comparison with the untreated plants and the numeral "5" indicating the complete inhibition or death of the test plants.

The compounds as shown in Table 5 were used for comparison.

TABLE 5

| Compound No. | Structure | Remarks |
|---|---|---|
| A | (phenyl-N-C(=O)-N(NH2)-CH=C-CH3 ring structure) | U.S. Pat. No. 3,920,653; Compound No. 19 |
| B | Cl,Cl,Cl-substituted phenyl-O-phenyl-NO2 | Chloronitrofen |

TEST EXAMPLE 1

Cylindrical plastic pots (diameter, 10 cm; height, 10 cm) were filled with upland field soil, and the seeds of Japanese millet, oats, tall morningglory and velvetleaf were sowed therein and covered with soil. A designated amount of the test compound formulated in an emulsifiable concentrate as in Formulation Example 2 was diluted with water, and the dilution was sprayed onto the soil surface by means of a small hand sprayer onto the soil surface by means of a small hand sprayer at a spray volume of 10 liters per are. The test plants were grown in a greenhouse for 20 days, and the herbicidal activity was examined. The results ar shown in Table 6.

TABLE 6

| Compound No. | Dosage (g/are) | Japanese millet | Oats | Tall morning-glory | Velvet-leaf |
|---|---|---|---|---|---|
| 1 | 5 | 5 | 5 | 5 | 5 |
|   | 1.25 | 5 | 5 | 5 | 5 |
| 2 | 5 | 5 | 5 | 5 | 5 |
|   | 1.25 | 5 | 5 | 5 | 5 |
| 3 | 5 | 5 | 5 | 5 | 5 |
|   | 1.25 | 5 | 5 | 5 | 5 |
| A | 1.25 | 0 | 0 | 0 | 0 |
| B | 2.5 | 0 | 0 | 0 | 0 |
|   | 1.25 | 0 | 0 | 0 | 0 |

TEST EXAMPLE 2

Cylindrical plastic pots (diameter, 10 cm; height, 10 cm) were filled with upland field soil, and the seeds of Japanese millet, tall morningglory, radish, velvetleaf and oats were sowed therein and cultivated in a greenhouse for 10 days. A designated amount of the test compound formulated in an emulsifiable concentrate as in Formulation Example 2 was diluted with water containing a spreading agent, and the dilution was sprayed over the foliage of the test plant by means of a small hand sprayer at a spray volume of 10 liters per are. The test plants were further grown in the greenhouse for 20 days, and the herbicidal activity was examined. The results are shown in Table 7.

TABLE 7

| Compound No. | Dosage (g/are) | Japanese millet | Tall morning-glory | Radish | Velvet-leaf | Oats |
|---|---|---|---|---|---|---|
| 1 | 10 | 5 | 5 | 5 | 5 | 5 |
|   | 1.25 | 5 | 5 | 5 | 5 | 5 |
| 2 | 10 | 5 | 5 | 5 | 5 | 5 |
|   | 1.25 | 5 | 5 | 5 | 5 | 5 |
| 3 | 10 | 5 | 5 | 5 | 5 | 5 |
|   | 1.25 | 5 | 5 | 5 | 5 | 5 |
| A | 1.25 | 0 | 0 | 0 | 0 | 0 |
| B | 1.25 | 0 | 0 | 0 | 0 | 0 |

TEST EXAMPLE 3

Vats (33 cm × 23 cm × 11 cm) were filled with upland field soil, and the seeds of rice plant, soybean, corn, tall morningglory, velvetleaf, black nightshade, johnsongrass and green foxtail were sowed therein in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 10 liter per are. The test plants were grown in a greenhouse for 20 days, and the herbicidal activity and phytotoxicity were examined. The results are shown in Table 8.

TABLE 8

| Compound No. | Dosage (g/a) | Phytotoxicity Rice plant | Corn | Soy-bean | Tall morning glory | Velvet leaf | Black night-shade | Johnson-grass | Green foxtail |
|---|---|---|---|---|---|---|---|---|---|
| 2 | 0.32 | 1 | 1 | 1 | — | 5 | 5 | 4 | 5 |
| 3 | 0.32 | 1 | 1 | 1 | 4 | 5 | 5 | — | 5 |
| A | 0.32 | 0 | 0 | 0 | 0 | 0 | 0 | 0 | 0 |
| B | 0.32 | 0 | 0 | 0 | 0 | 0 | 0 | 0 | 0 |

TEST EXAMPLE 4

Vats (33 cm × 23 cm × 11 cm) were filled with upland field soil, and the seeds of wheat, barley, pale smartweed, persian speedwell and field pansy were sowed therein in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 27 days, and the herbicidal activity and phytotoxicity were examined. The results are shown in Table 9.

TABLE 9

| Compound No. | Dosage (g/a) | Phytotoxicity Wheat | Barley | Pale smart-weed | Persian speed-well | Field pansy |
|---|---|---|---|---|---|---|
| 2 | 0.08 | 1 | 1 | 5 | 5 | 5 |
| 3 | 0.08 | 1 | 1 | 5 | 5 | 5 |
| A | 0.08 | 0 | 0 | 0 | 0 | 0 |
| B | 0.08 | 0 | 0 | 0 | 0 | 0 |

TEST EXAMPLE 5

Vats (33 cm × 23 cm × 11 cm) were filled with upland field soil, and the seeds of wheat, barley, pale smartweed, catchweed bedstraw, common chickweed, persian speedwell and field pansy were sowed therein and cultivated for 25 days in a greenhouse. A designated amount of the test compound formulated in an emulsifiable concentrate as in Formulation Example 2 was diluted with water, and the dilution was sprayed over the foliage of the test plants by means of a small hand sprayer at a spray volume of 10 liters per are. The test plants were further grown in the greenhouse for 27 days, and the herbicidal activity and phytotoxicity were examined. At the time of the application, the test plants were generally at the 1 to 4 leaf stage and in 2 to 12 cm height, although the growing stage of the test plants varied depending on their species. The results are shown in Table 10.

TABLE 10

| Compound No. | Dosage (g/a) | Phytotoxicity Wheat | Barley | Pale smart-weed | Catch weed bedstraw | Common chick weed | Persian speed-well | Field pansy |
|---|---|---|---|---|---|---|---|---|
| 3 | 0.08 | 1 | 1 | 5 | 5 | 4 | 5 | 5 |
| A | 0.08 | 0 | 0 | 0 | 0 | 0 | 0 | 0 |

TABLE 10-continued

| Compound No. | Dosage (g/a) | Phytotoxicity | | Herbicidal activity | | | | |
|---|---|---|---|---|---|---|---|---|
| | | Wheat | Barley | Pale smart-weed | Catch weed bedstraw | Common chick weed | Persian speed-well | Field pansy |
| B | 0.08 | 0 | 0 | 0 | 0 | 0 | 0 | 0 |

TEST EXAMPLE 6

Vats (33 cm×23 cm×11 cm) were filled with upland field soil, and the seeds of barnyardgrass, johnsongrass, green foxtail, large crabgrass were sowed therein in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 20 days, and the herbicidal activity was examined. The results are shown in Table 11.

TABLE 11

| Compound No. | Dosage (g/a) | Herbicidal activity | | | |
|---|---|---|---|---|---|
| | | Barn-yard-grass | Johnson-grass | Green foxtail | Large crab-grass |
| 1 | 5 | 5 | 5 | 5 | 5 |
| 2 | 5 | 5 | 5 | 5 | 5 |
| 3 | 5 | 5 | 5 | 5 | 5 |

TEST EXAMPLE 7

Vats (33 cm×23 cm×11 cm) were filled with upland field soil, and the seeds of corn, common cocklebur, velvetleaf, tall morningglory, sicklepod, black nightshade, barnyardgrass and johnsongrass were sowed therein and cultivated for 18 days in a greenhouse. A designated amount of the test compound formulated in an emulsifiable concentrate as in Formulation Example 2 was diluted with water, and the dilution was sprayed over the foliage of the test plants by means of a small hand sprayer at a spray volume of 10 liters per are. The test plants were further grown in the greenhouse for 20 days, and the herbicidal activity and phytotoxicity were examined. At the time of the application, the test plants were generally at the 1 to 4 leaf stage and in 2 to 12 cm height, although the growing stage of the test plants varied depending on their species. The results are shown in Table 12.

TABLE 12

| Compound No. | Dosage (g/a) | Phyto-toxicity Corn | Herbicidal activity | | | | | | |
|---|---|---|---|---|---|---|---|---|---|
| | | | Common-cocklebur | Velvet-leaf | Tall morning-glory | Sickle-pod | Black night-shade | Barn-yard grass | Johnson-grass |
| 2 | 0.08 | 1 | 5 | 5 | 5 | 5 | 5 | 5 | — |
| 3 | 0.08 | 1 | 5 | 5 | 5 | 5 | 5 | 5 | 4 |
| B | 0.08 | 0 | 0 | 0 | 0 | 0 | 0 | 0 | 0 |

What is claimed is:

1. A compound of the formula:

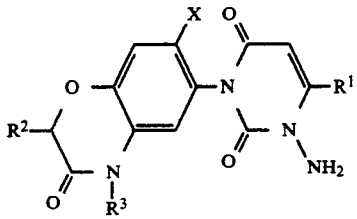

wherein $R^1$ is a trifluoromethyl group or a pentafluoroethyl group, $R^2$ is a hydrogen atom or a methyl group, $R^3$ is a $C_1$–$C_7$ alkyl group, a $C_3$–$C_7$ alkenyl group, or a $C_3$–$C_7$ alkynyl group, and X is a hydrogen atom or a fluorine atom.

2. The compound according to claim 1, wherein $R^2$ is a hydrogen atom, $R^3$ is a $C_3$–$C_4$ alkynyl group and X is a fluorine atom.

3. The compound according to claim 1, which is 3-amino-1-[7-fluoro-4-propargyl-2H-1,4-benzoxazin-3(4H)-on-6-yl]-4-trifluoromethyl-1,2,3,6-tetrahydropyrimidine-2,6-dione.

4. The compound according to claim 1, which is 3-amino-1-[7-fluoro-4-(1-methylpropargyl)-2H-1,4-benzoxazin-3(4H)-on-6-yl]-4-trifluoromethyl-1,2,3,6-tetrahydropyrimidine-2,6-dione.

5. The compound according to claim 1, which is 3-amino-1-[7-fluoro-4-(n-propyl)-2H-1,4-benzoxazin-3(4H)-on-6-yl]-4-trifluoromethyl-1,2,3,6-tetrahydropyrimidine-2,6-dione.

6. The compound according to claim 1, wherein $R_3$ is selected from the group consisting of $CH_2CH$=$CH_2$,

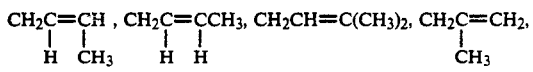

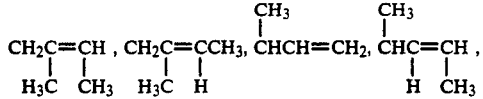

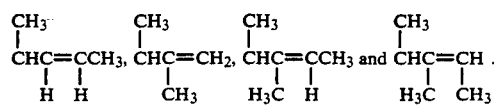

7. A herbicidal composition which comprises as an active ingredient a herbicidally effective amount of the compound according to claim 1, and an inert carrier or diluent.

8. A method for exterminating harmful weeds, which comprises applying a herbicidally effective amount of the compound according to claim 1 and an inert carrier or diluent to the area where the undesired weeds grow or will grow.

9. The compound according to claim 1, wherein $R_3$ is selected from the group consisting of $CH_2C\equiv CH$,

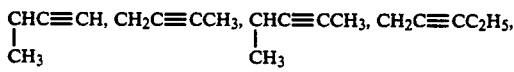

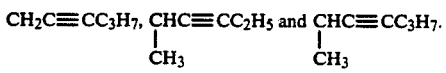

10. A herbicidal composition which comprises as an active ingredient a herbicidally effective amount of the compound according to claim 2, and an inert carrier or diluent.

11. A herbicidal composition which comprises as an active ingredient a herbicidally effective amount of the compound according to claim 3, and an inert carrier or diluent.

12. A herbicidal composition which comprises as an active ingredient a herbicidally effective amount of the compound according to claim 4, and an inert carrier or diluent.

13. A herbicidal composition which comprises as an active ingredient a herbicidally effective amount of the compound according to claim 5, and an inert carrier or diluent.

14. A method for exterminating harmful weeds, which comprises applying a herbicidally effective amount of the compounds according to claim 2 and an inert carrier or diluent to the area where the undesired weeds grow or will grow.

15. A method for exterminating harmful weeds, which comprises applying a herbicidally effective amount of the compounds according to claim 3 and an inert carrier or diluent to the area where the undesired weeds grow or will grow.

16. A method for exterminating harmful weeds, which comprises applying a herbicidally effective amount of the compounds according to claim 4 and an inert carrier or diluent to the area where the undesired weeds grow or will grow.

17. A method for exterminating harmful weeds, which comprises applying a herbicidally effective amount of the compounds according to claim 5 and an inert carrier or diluent to the area where the undesired weeds grow or will grow.

18. The compound according to claim 1, wherein $R_3$ is selected from the group consisting of $CH_3$, $C_2H_5$, $(n)-C_3H_7$, $(i)-C_3H_7$, $(n)-C_4H_9$, $(s)-C_4H_9$, $(i)-C_4H_9$, $(n)-C_5H_{11}$, $(n)-C_6H_{13}$, and $(n)-C_7H_{15}$.

* * * * *